US010697965B2

(12) United States Patent
Cartron et al.

(10) Patent No.: US 10,697,965 B2
(45) Date of Patent: Jun. 30, 2020

(54) METHOD FOR TREATING AND PROGNOSING CANCER

(71) Applicants: INSERM (INSITUT NATIONAL DE LA SANTE ET DE LA RECHERCHE MEDICALE), Paris (FR); UNIVERSITE DE NANTES, Nantes (FR); UNIVERSITE D'ANGERS, Angers (FR); CENTRE NATIONAL DE LA RECHERCHE SCIENTIFIQUE (CNRS), Paris (FR)

(72) Inventors: Pierre-Francois Cartron, Nantes (FR); Mathilde Cheray, Stockholm (SE); Francois Valette, Nantes (FR)

(73) Assignees: INSERM (INSITUT NATIONAL DE LA SANTE ET DE LA RECHERCHE MEDICALE), Paris (FR); UNIVERSITE DE NANTES, Nantes (FR); UNIVERSITE D'ANGERS, Angers (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/554,599

(22) PCT Filed: Mar. 1, 2016

(86) PCT No.: PCT/EP2016/054288
§ 371 (c)(1),
(2) Date: Aug. 30, 2017

(87) PCT Pub. No.: WO2016/139192
PCT Pub. Date: Sep. 9, 2016

(65) Prior Publication Data
US 2018/0238885 A1    Aug. 23, 2018

(30) Foreign Application Priority Data

Mar. 2, 2015    (EP) .................................... 15305314

(51) Int. Cl.
*A61K 38/00*    (2006.01)
*G01N 33/574*    (2006.01)
*C07K 7/08*    (2006.01)
*C12Q 1/6886*    (2018.01)
*A61P 35/00*    (2006.01)
*A61K 38/10*    (2006.01)
*A61K 45/06*    (2006.01)
*G01N 33/50*    (2006.01)

(52) U.S. Cl.
CPC ....... *G01N 33/57407* (2013.01); *A61K 38/00* (2013.01); *A61K 38/10* (2013.01); *A61K 45/06* (2013.01); *A61P 35/00* (2018.01); *C07K 7/08* (2013.01); *C12Q 1/6886* (2013.01); *G01N 33/5011* (2013.01); *C12Q 2600/106* (2013.01); *C12Q 2600/118* (2013.01); *C12Q 2600/158* (2013.01); *G01N 2333/4706* (2013.01); *G01N 2333/91017* (2013.01); *G01N 2500/04* (2013.01); *G01N 2800/52* (2013.01)

(58) Field of Classification Search
CPC ........ A61K 38/00; A61K 38/10; A61K 45/00; A61K 45/06; G01N 33/57407; G01N 33/5011; G01N 2500/04; G01N 2333/91017; G01N 2333/4706; G01N 2800/52; A61P 35/00; C12Q 1/6886; C12Q 2600/118; C12Q 2600/106; C12Q 2600/158; C07K 7/08
USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3; 530/300
See application file for complete search history.

(56) References Cited

U.S. PATENT DOCUMENTS

2006/0084053 A1 * 4/2006 Li ........................ C12N 9/1007
435/6.12

OTHER PUBLICATIONS

McNamara et al, Cancers, vol. 5, pp. 1103-1119 (Year: 2013).*
Stupp et al, The New England Journal of Medicine, vol. 352, pp. 987-996 (Year: 2005).*
Etcheverry et al, BMC Genomics, vol. 11, 11 pages (Year: 2010).*
Wu et al, Journal of Neuroscience Research, vol. 90, pp. 1883-1891 (Year: 2012).*
Banelli et al, International Journal of Genomic, vol. 2017, 16 pages (Year: 2017).*
Anonymous: "M1T192", Retrieved from the Internet: URL:http://www.uniprot.org/uniprot/M1T192, May 1, 2013.
Mairead McNamara et al: "Emerging Biomarkers in Glioblastoma", Cancers, vol. 5, No. 3, pp. 1103-1119, Aug. 22, 2013.

(Continued)

*Primary Examiner* — D. L. Jones
(74) *Attorney, Agent, or Firm* — W&C IP

(57) ABSTRACT

The present invention relates to an in vitro method for determine the prognosis of the survival time of a patient suffering from a cancer comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value. The invention also relates to a compound which is a DNMT3A/ISGF3γ antagonist or a compound which is a DNMT3A/ISGF3γ gene expression inhibitor for use in the treatment and prevention of cancer.

5 Claims, 3 Drawing Sheets
Specification includes a Sequence Listing.

(56) References Cited

OTHER PUBLICATIONS

Eric Hervouet et al: "Dnmt3/transcription factor interactions as crucial players in targeted DNA methylation", Epigenetics, vol. 4, No. 7, pp. 487-499, Oct. 1, 2009.

E Hervouet et al: Impact of the DNA methyltransferases expression on the methylation status of apoptosis-associated genes in glioblastoma multiforme:, Cell Death and Disease, vol. 1, No. 1, p. e8, Oct. 1, 2010.

* cited by examiner

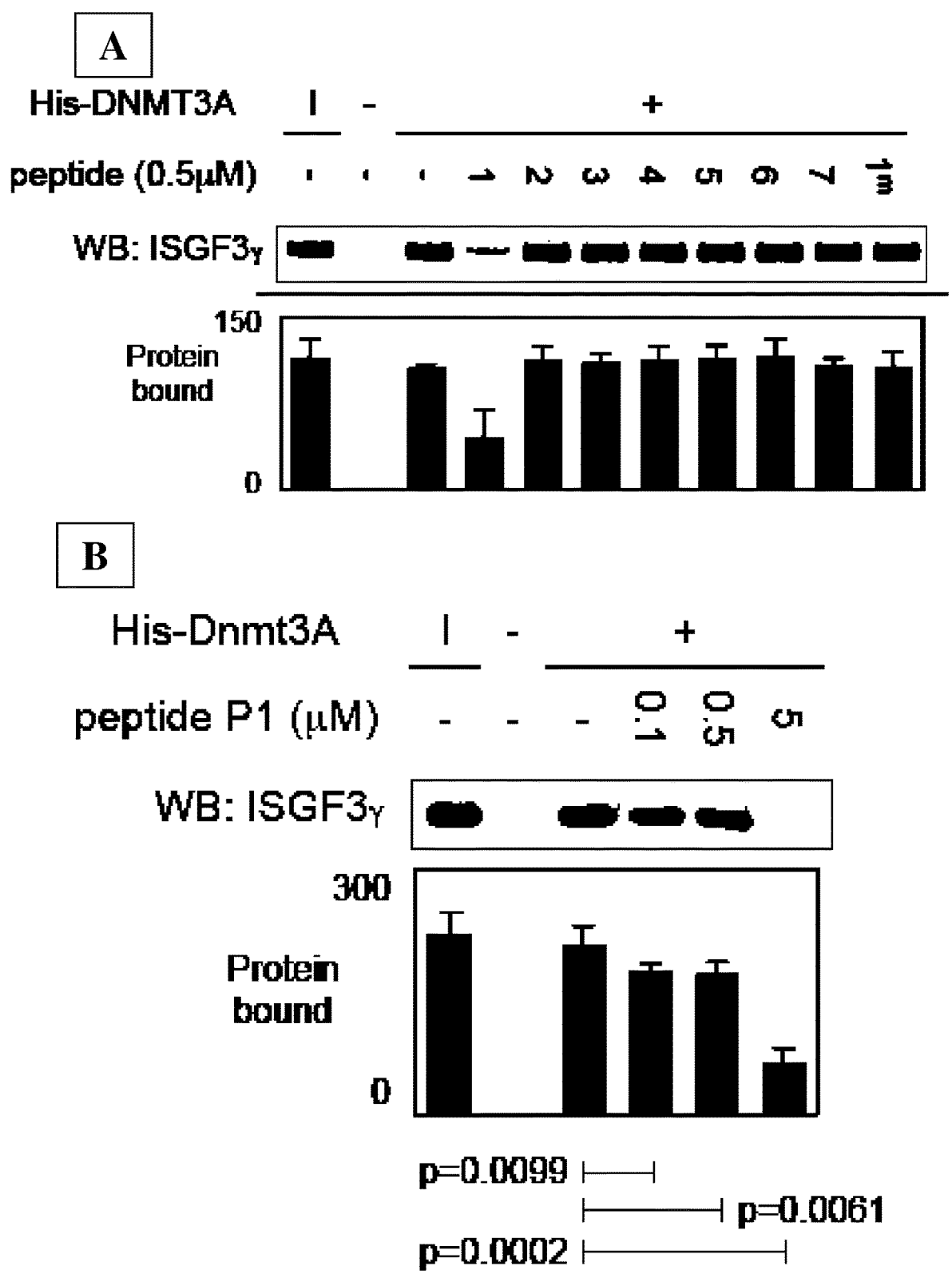
Figure 2 A and B

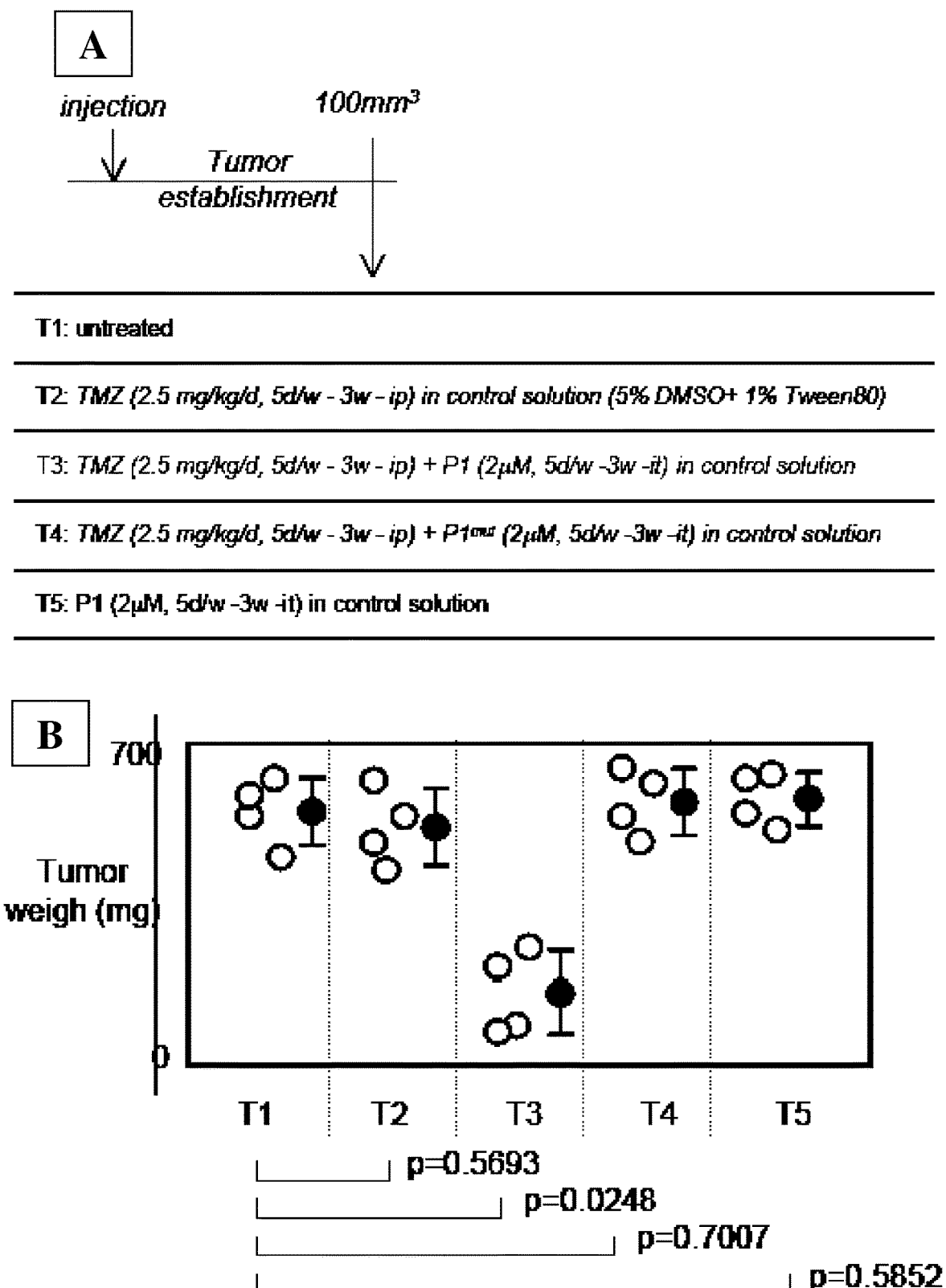
Figure 3 A and B

METHOD FOR TREATING AND PROGNOSING CANCER

FIELD OF THE INVENTION

The present invention relates to an in vitro method for determine the prognosis of the survival time of a patient suffering from a cancer comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

The invention also relates a compound which is a DNMT3A/ISGF3γ antagonist or a compound which is a DNMT3A/ISGF3γ gene expression inhibitor for use in the treatment and prevention of cancer.

BACKGROUND OF THE INVENTION

DNA methylation patterns are frequently aberrant in cancer cells. Thus, hypomethylation of intergenic regions can occur, leading to tumorigenesis via the activation of transposable elements and increased genomic instability. Local hypomethylation of genes promoters can promote oncogene expression, while local hypermethylation of the genes promoters can lead to loss of tumor suppressor function in cancer cells. Based on this last point, drug development has focused on DNA methylation inhibitors with the goal of activating tumor suppressor genes (TSG) silenced by DNA methylation. But in absence of specificity, a DNMT inhibitor can promote the demethylation of TSG but also of oncogenes and transposable elements. Thus, the use of unspecific DNMT inhibitors can be anti-tumorigenic or pro-tumorigenic. Besides, this last point is illustrated in several articles. Indeed, literature reports that 5-aza-2'-deoxycytidine treatment (an unspecific DNMT inhibitor) increased the invasiveness of non-invasive breast cancer cell lines MCF-7 cells and ZR-75-1 and dramatically induced pro-metastatic genes [Chik F et al., 2011]. 5-aza-2'-deoxycytidine treatment is also reported as an inducer of glioma from astrocytes and as an enhancer of tumorigenic property of glioma cells. Nevertheless, 5-aza-2'-deoxycytidine is approved by the Food and Drug Administration of the United States for the myelodysplastic syndrome treatment, where it demonstrates significant, although usually transient, improvement in patient survival. Despite this undoubtable clinical utility, the dual effect of the use of unspecific DNMT inhibitors provides evidence for the development of specific DNMT inhibitors. In addition, specific DNMT inhibitors could also allow targeting of tumors harboring an aberrant functionality of a particular DNMT. The development of specific DNMT inhibitors could also reduced off-target effects associated with the use of unspecific DNMT inhibitors.

At present, several molecules are developed to specifically target a particular DNMT. Thus, DNMT1 can be inhibited by using RG108, MG98 or Procainamide, DNMT3A while DNMT3B can be specifically inhibited by using Theaflavin 3, 3'-digallate or NanaomycinA, respectively [Amato R et al., 2012; Kuck D et al., 2010; Kuck D et al., 2010; Lee B et al., 2005 and Rajavelu A et al., 2001]. To identify these specific DNMT inhibitors, several strategies are developed: the docking-based virtual screening methods, the screening of natural products, the design and generation of derivatives of DNMT inhibitors already known, the molecular modeling of DNMT inhibitors by using crystal structure studies of DNMTs, or the design of siRNA targeting DNMTs [Kuck D et al., 2010; Medina-Franco J et al., 2011; Suzuki T et al., 2010; Yoo J et al., 2012; Yoo J et al., 2012 and Venza M et al., 2013]. In a recent article, we demonstrated that DNMT inhibitors can be also addressed against a specific DNMT/protein-x interaction [Cheray M et al., 2013].

SUMMARY OF THE INVENTION

In the present study, the inventors asked the question to know whether the presence of interaction existing between DNMT3A and a DNMT3A-binding protein (D3A-BP) permit to identify a subpopulation of patients suffering from glioblastoma multiformes (GBM) harboring a shorter overall survival time and whose the glioma cells presented a resistance phenotype to the temozolomide/irradiation treatment. Then, they wanted to know whether it's possible to develop a strategy aiming to specifically inhibit the DNMT3A/D3A-BP interaction associated with a poor prognosis of survival and/or response to the temozolomide/irradiation treatment in order to increase the percentage of the temozolomide+irradiation-induced cell death, and the sensitivity of TMZ in a mice model of gliomagenesis.

Thus, the present invention relates to an in vitro method for determine the prognosis of the survival time of a patient suffering from a cancer comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

The invention also relates a compound which is a DNMT3A/ISGF3γ antagonist or a compound which is a DNMT3A/ISGF3γ gene expression inhibitor for use in the treatment and prevention of cancer.

DETAILED DESCRIPTION OF THE INVENTION

Prognostic and Predictive Methods

The first aspect of the invention relates to an in vitro method for determining the prognosis of the survival time of a patient suffering from a cancer comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

The invention also relates to an in vitro method for predicting the survival time of a patient suffering from a cancer and treated with conventional treatment comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

The invention also relates to an in vitro method for predicting the response of a patient suffering from a cancer and treated with conventional treatment comprising the steps consisting of i) determining the expression level of the couple DNMT3A/ISGF3γ in a sample from said patient, ii) comparing said expression level with a predetermined reference value and iii) providing a good response when the expression level is lower than the predetermined reference value and a poor response when the expression level is higher than the predetermined reference value.

As used herein, the terms "conventional treatment" denote any compounds, combination of compounds, combination of chemotherapeutic treatment and radiotherapeutic agent and combination of chemotherapeutic treatment and radiation which may be used for the treatment of cancer. For example, in the case of the treatment of glioblastoma, the conventional treatment may the use of a combination of the temozolomide and radiation.

Thus, the invention also relates to a method for predicting the survival time of a patient suffering from a glioblastoma and treated with radiation and temozolomide comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

The invention also relates to a method for predicting the response of a patient suffering from a glioblastoma and treated with radiation and temozolomide comprising the steps consisting of i) determining the expression level of the couple DNMT3A/ISGF3γ in a sample from said patient, ii) comparing said expression level with a predetermined reference value and iii) providing a good response when the expression level is lower than the predetermined reference value and a poor response when the expression level is higher than the predetermined reference value.

In one embodiment, the cancer may be any solid or liquid cancer. Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, glioblastoma, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In a particular embodiment, the glioblastoma is a glioblastoma multiforme.

Typically, the sample according to the invention may be a blood, plasma, serum sample or a cancer biopsy. In a particular embodiment, said sample is a glioblastoma biopsy.

As used herein, the term "DNMT3A" for "DNA methyltransferase 3A" (Entrez Gene ID number: 1788; mRNA sequence reference: NM_022552.4; protein sequence reference: Q9Y6K1) designed a de novo DNA methyltransferase i.e. an enzyme responsible for the establishment of de novo genomic DNA methylation patterns and, as such, involved in normal development as well as in many diseases including cancer.

Protein sequence of DNMT3A (SEQ ID NO:3) is:

MPAMPSSGPGDTSSSAAEREEDRKDGEEQEEPRGKEERQEPSTTARKVGR

PGRKRKHPPVESGDTPKDPAVISKSPSMAQDSGASELLPNGDLEKRSEPQ

PEEGSPAGGQKGGAPAEGEGAAETLPEASRAVENGCCTPKEGRGAPAEAG

KEQKETNIESMKMEGSRGRLRGGLGWESSLRQRPMPRLTFQAGDPYYISK

RKRDEWLARWKREAEKKAKVIAGMNAVEENQGPGESQKVEEASPPAVQQP

TDPASPTVATTPEPVGSDAGDKNATKAGDDEPEYEDGRGFGIGELVWGKL

RGFSWWPGRIVSWWMTGRSRAAEGTRWVMWFGDGKFSVVCVEKLMPLSSF

CSAFHQATYNKQPMYRKAIYEVLQVASSRAGKLFPVCHDSDESDTAKAVE

VQNKPMIEWALGGFQPSGPKGLEPPEEEKNPYKEVYTDMWVEPEAAAYAP

PPPAKKPRKSTAEKPKVKEIIDERTRERLVYEVRQKCRNIEDICISCGSL

NVTLEHPLFVGGMCQNCKNCFLECAYQYDDDGYQSYCTICCGGREVLMCG

NNNCCRCFCVECVDLLVGPGAAQAAIKEDPWNCYMCGHKGTYGLLRRRED

WPSRLQMFFANNHDQEFDPPKVYPPVPAEKRKPIRVLSLFDGIATGLLVL

KDLGIQVDRYIASEVCEDSITVGMVRHQGKIMYVGDVRSVTQKHIQEWGP

FDLVIGGSPCNDLSIVNPARKGLYEGTGRLFFEFYRLLHDARPKEGDDRP

FFWLFENVVAMGVSDKRDISRFLESNPVMIDAKEVSAAHRARYFWGNLPG

MNRPLASTVNDKLELQECLEHGRIAKFSKVRTITTRSNSIKQGKDQHFPV

FMNEKEDILWCTEMERVFGFPVHYTDVSNMSRLARQRLLGRSWSVPVIRH

LFAPLKEYFACV

As used herein, the term "ISGF3γ" (Entrez Gene ID number: 10379; mRNA sequence reference: NM_006084.4; protein sequence reference: Q00978) denotes a Transcription factor that mediates signaling by type I IFNs. ISGF3γ binds to the IFN stimulated response element (ISRE) to activate the transcription of interferon stimulated genes, which drive the cell in an antiviral state.

In another embodiment, the invention relates to an in vitro method for determine the prognosis of the overall survival (OS) of a patient suffering from a cancer comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

In another embodiment, the invention also relates to a method for predicting the overall survival (OS) of a patient suffering from a cancer and treated with conventional treatment comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

In another embodiment, the invention also relates to a method for predicting the overall survival (OS) of a patient suffering from a glioblastoma and treated with radiation and temozolomide comprising the steps consisting of i) determining the expression level of the couple DNMT3A/ISGF3γ in a sample from said patient, ii) comparing said expression level with a predetermined reference value and iii) providing a good prognosis when the expression level is lower than the predetermined reference value and a poor prognosis when the expression level is higher than the predetermined reference value.

As used herein, the term "Overall survival (OS)" denotes the percentage of people in a study or treatment group who are still alive for a certain period of time after they were diagnosed with or started treatment for a disease, such as a cancer (according to the invention).

As used herein, the term "Good Prognosis" denotes a patient with more than 50% chance of survival for the next 3 years after the treatment.

The invention also relates to a method for predicting the responsiveness of a patient affected with a glioblastoma to a temozolomide and radiation treatment comprising the steps consisting of i) determining the expression level of the couple DNMT3A/ISGF3γ in a sample from said patient ii) comparing the expression level determined at step i) with its predetermined reference value wherein when the expression level determined at step i) is lower than its predetermined reference values then the responsiveness of the patient to the treatment is good, and when the expression level determined at step i) is higher than its predetermined reference value then the responsiveness of the patient to the treatment is bad.

In one embodiment and according to the methods of the invention, the determination of the expression level of the couple DNMT3A/ISGF3γ may be determined before or after the beginning of the treatment of the patient.

In another embodiment, the patient affected with a glioblastoma is mainly treated with a standard treatment consisting of maximal surgical resection, radiotherapy, and concomitant adjuvant chemotherapy with temozolomide.

The term "determining the expression level of" as used above includes qualitative and/or quantitative detection (measuring levels) with or without reference to a control. Typically expression level of the couple DNMT3A/ISGF3γ may be measured for example by enzyme-labeled and mediated immunoassays (such as ELISA), flow cytometry assessment or qRT-PCR performed on the sample.

The "reference value" may be a healthy subject, i.e. a subject who does not suffer from any cancer and particularly glioblastoma. Particularly, said control is a healthy subject.

Detection of the expression level of the couple DNMT3A/ISGF3γ in the sample may be performed by measuring the level of DNMT3A/ISGF3γ proteins or the DNMT3A/ISGF3γ genes.

In the case of the detection of DNMT3A/ISGF3γ proteins, the methods may comprise contacting a sample with a binding partner capable of selectively interacting with DNMT3A/ISGF3γ proteins present in the sample. The binding partner is generally an antibody that may be polyclonal or monoclonal, particularly monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against the proteins to be tested. A sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule is added. The secondary binding molecule is allowed to react with any captured sample marker protein, the plate is washed and the presence of the secondary binding molecule is detected using methods well known in the art.

Various immunoenzymatic staining methods are known in the art for detecting a protein of interest. For example, immunoenzymatic interactions can be visualized using different enzymes such as peroxidase, alkaline phosphatase, or different chromogens such as DAB, AEC, or Fast Red; or fluorescent labels such as FITC, Cy3, Cy5, Cy7, Alexafluors, etc. Counterstains may include H&E, DAPI, Hoechst, so long as such stains are compatable with other detection reagents and the visualization strategy used. As known in the art, amplification reagents may be used to intensify staining signal. For example, tyramide reagents may be used. The staining methods of the present invention may be accomplished using any suitable method or system as would be apparent to one of skill in the art, including automated, semi-automated or manual systems.

The method of the invention may comprise a further step consisting of comparing DNMT3A/ISGF3γ proteins expression with a control reference.

In the case of detection of the DNMT3A/ISGF3γ genes, the term "expression level of DNMT3A/ISGF3γ" refers to an amount or a concentration of a transcription product, for instance mRNA coding for DNMT3A/ISGF3γ genes. Typically, a level of mRNA expression can be expressed in units such as transcripts per cell or nanograms per microgram of tissue. A level of protein can be expressed as nanograms per microgram of tissue or nanograms per milliliter of a culture medium, for example. Alternatively, relative units can be employed to describe an expression level.

Measuring the expression level of a gene can be performed by a variety of techniques well known in the art.

Typically, the expression level of a gene may be determined by determining the quantity of mRNA. Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e. g., Northern blot analysis, in situ hybridization) and/or amplification (e.g., RT-PCR).

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more particularly 85% identical and even more particularly 90-95% identical. In certain embodiments, it will be advantageous to use nucleic acids in combination with appropriate means, such as a detectable label, for detecting hybridization.

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, antllranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6di-clllorotriazin-2-yDarninofluorescein (DTAF), 2'7'dimethoxy-4'5'-dichloro-6-carboxyfluorescein (JOE), fluorescein, fluorescein isothiocyanate (FITC), and QFITC Q (RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716, 979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., Science 281:20132016, 1998; Chan et al., Science 281:2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif.).

Additional labels include, for example, radioisotopes (such as 3H), metal chelates such as DOTA and DPTA chelates of radioactive or paramagnetic metal ions like Gd3+, and liposomes.

Detectable labels that can be used with nucleic acid molecules also include enzymes, for example horseradish peroxidase, alkaline phosphatase, acid phosphatase, glucose oxidase, beta-galactosidase, beta-glucuronidase, or beta-lactamase.

Alternatively, an enzyme can be used in a metallographic detection scheme. For example, silver in situ hybridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redoxactive agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH).

In situ hybridization (ISH) involves contacting a sample containing target nucleic acid sequence (e.g., genomic target nucleic acid sequence) in the context of a metaphase or interphase chromosome preparation (such as a cell or tissue sample mounted on a slide) with a labeled probe specifically hybridizable or specific for the target nucleic acid sequence (e.g., genomic target nucleic acid sequence). The slides are optionally pretreated, e.g., to remove paraffin or other materials that can interfere with uniform hybridization. The sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the chromosome target is performed using standard techniques.

For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin. Amplification of the FITC signal can be effected, if necessary, by incubation with biotin-conjugated goat antiavidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). For a general description of in situ hybridization procedures, see, e.g., U.S. Pat. No. 4,888,278.

Numerous procedures for FISH, CISH, and SISH are known in the art. For example, procedures for performing FISH are described in U.S. Pat. Nos. 5,447,841; 5,472,842; and 5,427,932; and for example, in Pirlkel et al., Proc. Natl. Acad. Sci. 83:2934-2938, 1986; Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. 1. Pathol. 157:1467-1472, 2000 and U.S. Pat. No. 6,942,970. Additional detection methods are provided in U.S. Pat. No. 6,280,929.

Numerous reagents and detection schemes can be employed in conjunction with FISH, CISH, and SISH procedures to improve sensitivity, resolution, or other desirable properties. As discussed above probes labeled with fluorophores (including fluorescent dyes and QUANTUM DOTS®) can be directly optically detected when performing FISH. Alternatively, the probe can be labeled with a non-fluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., QUANTUM DOT®) or with another indirectly detectable moiety, or can be contacted with one or more additional specific binding agents (e.g., secondary or specific antibodies), which can be labeled with a fluorophore.

In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2007/01 17153.

It will be appreciated by those of skill in the art that by appropriately selecting labelled probe-specific binding agent pairs, multiplex detection schemes can be produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can be labelled with a first hapten, such as biotin, while a second probe that corresponds to a second target sequence can be labelled with a second hapten, such as DNP. Following exposure of the sample to the probes, the bound probes can be detected by contacting the sample with a first specific binding agent (in this case avidin labelled with a first fluorophore, for example, a first spectrally distinct QUANTUM DOT®, e.g., that emits at 585 mn) and a second specific binding agent (in this case an anti-DNP antibody, or antibody fragment, labelled with a second fluorophore (for example, a second spectrally distinct QUANTUM DOT®, e.g., that emits at 705 mn). Additional probes/binding agent pairs can be added to the multiplex detection scheme using other spectrally distinct fluorophores. Numerous variations of direct, and indirect (one step, two step or more) can be envisioned, all of which are suitable in the context of the disclosed probes and assays.

Probes typically comprise single-stranded nucleic acids of between 10 to 1000 nucleotides in length, for instance of between 10 and 800, more particularly of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they particularly hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A particular kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from cumulus cells and subjecting the RNAs to amplification and hybridization to specific probes, more particularly by means of a quantitative or semi-quantitative RT-PCR.

In another particular embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

Expression level of a gene may be expressed as absolute expression level or normalized expression level. Typically, expression levels are normalized by correcting the absolute expression level of a gene by comparing its expression to the expression of a gene that is not a relevant for determining the cancer stage of the patient, e.g., a housekeeping gene that is constitutively expressed. Suitable genes for normalization include housekeeping genes such as the actin gene ACTB, ribosomal 18S gene, GUSB, PGK1 and TFRC. According to the invention the housekeeping genes used were GAPDH, GUSB, TBP and ABL1. This normalization allows the comparison of the expression level in one sample, e.g., a patient sample, to another sample, or between samples from different sources.

Typically, a "threshold value", "threshold level", "reference value" or "cut-off value" can be determined experimentally, empirically, or theoretically. A threshold value can also be arbitrarily selected based upon the existing experimental and/or clinical conditions, as would be recognized by a person of ordinary skilled in the art. Particularly, the person skilled in the art may compare the expression levels of the couple DNMT3A/ISGF3γ obtained according to the method of the invention with a defined threshold value.

Particularly, said threshold value is the mean expression level of the couple DNMT3A/ISGF3γ of a population of healthy individuals. As used herein, the term "healthy individual" denotes a human which is known to be healthy, i.e. which does not suffer from a cancer and in particular from a glioblastoma and does not need any medical care.

Typically, the skilled person in the art may determine the expression level of the couple DNMT3A/ISGF3γ in a biological sample, particularly a biopsy of a glioblastoma cancer for example, of 100 individuals known to be healthy. The mean value of the obtained expression levels is then determined, according to well known statistical analysis, so as to obtain the mean expression level of the couple DNMT3A/ISGF3γ. Said value is then considered as being normal and thus constitutes a threshold value. By comparing the expression levels of the couple DNMT3A/ISGF3γ to this threshold value, the physician is then able to classify and prognostic the cancer.

Accordingly, the physician would be able to adapt and optimize appropriate medical care of a subject in a critical and life-threatening condition suffering from cancer. The determination of said prognosis is highly appropriate for follow-up care and clinical decision making.

The present invention also relates to kits useful for the methods of the invention, comprising means for detecting DNMT3A/ISGF3γ expression.

According to the invention, the kits of the invention may comprise an anti-DNMT3A protein antibody and an anti-ISGF3γ; and another molecule coupled with a signalling system which binds to said DNMT3A/ISGF3γ antibodies or any molecule which bind to the mRNA of DNMT3A/ISGF3γ genes like a probe.

Typically, the antibodies or combination of antibodies are in the form of solutions ready for use. In one embodiment, the kit comprises containers with the solutions ready for use. Any other forms are encompassed by the present invention and the man skilled in the art can routinely adapt the form to the use in immunohistochemistry.

In another embodiment, the invention relates to an in vitro method for monitoring a patient's response cancer treatment which comprises a step of measuring the expression level of the couple DNMT3A/ISGF3γ, in a sample from a patient.

Thus, the present invention relates to the use of the couple DNMT3A/ISGF3γ as a biomarker for the monitoring of anti-cancer therapies and more particularly an anti-glioblastoma therapy.

Another aspect of the invention relates to a compound which is an antagonist of the couple DNMT3A/ISGF3γ or an inhibitor of the expression of the couple DNMT3A/ISGF3γ for use in the treatment of patient suffering of a cancer with a high expression level of the couple DNMT3A/ISGF3γ.

Particularly, the invention also relates to a compound which is an antagonist of the couple DNMT3A/ISGF3γ or an inhibitor of the expression of the couple DNMT3A/ISGF3γ for use in the treatment of patient suffering from a glioblastoma with a high expression level of the couple DNMT3A/ISGF3γ.

Therapeutic Method

A second aspect of the invention relates to a compound which is a DNMT3A/ISGF3γ antagonist or a compound which is a DNMT3A/ISGF3γ gene expression inhibitor for use in the treatment and prevention of cancer.

By "DNMT3A/ISGF3γ antagonist" is meant a natural or synthetic compound that has a biological effect opposite to that of a natural ligand of DNMT3A and/or ISGF3γ. According to the invention, the antagonist binds to the couple DNMT3A/ISGF3γ and blocks the action of these proteins by competing with the ligand of these proteins. An antagonist is defined by its ability to block the actions of a natural ligand. The term "DNMT3A/ISGF3γ antagonist" refers to any DNMT3A/ISGF3γ antagonist that is currently known in the art or that will be identified in the future, and includes any chemical entity that, upon administration to a subject, results in inhibition of a biological activity associated with activation of the DNMT3A/ISGF3γ proteins in the subject, including any of the downstream biological effects otherwise resulting from the binding to DNMT3A/ISGF3γ of its natural ligands. Alternatively, such an antagonist can act by occupying the ligand binding site or a portion thereof of DNMT3A/ISGF3γ proteins, thereby making the receptor inaccessible to its natural ligand so that its normal biological activity is prevented or reduced. In one embodiment, the antagonist of the invention can block the binding of the protein DNMT3A to the protein ISGF3γ. Thus, a "DNMT3A/ISGF3γ antagonist" can be a compound which binds to the DNMT3A protein or to the ISGF3γ protein.

According to the invention, a DNMT3A/ISGF3γ antagonist may bind to the DNMT3A protein at the position 85-99, 103-129, 178-207, 235-246, 256-273, 331-360, 409-433 or 547-574 of SEQ ID NO: 3 and inhibits the DNMT3A/ISGF3γ interaction.

Thus, the present invention also relates to a method of screening a candidate compound for use as a drug for the prevention and treatment of cancer in a subject in need thereof, wherein the method comprises the steps of: i) providing candidate compounds and ii) selecting candidate compounds that block or antagonise DNMT3A/ISGF3γ.

In a further aspect, the present invention relates to a method of screening a candidate compound for use as a drug for the treatment and prevention of cancer in a subject in need thereof, wherein the method comprises the steps of:
(i) providing the couple DNMT3A/ISGF3γ, providing a cell, tissue sample or organism expressing DNMT3A/ISGF3γ,
(ii) providing a candidate compound such as small organic molecule, intra-antibodies, peptide or polypeptide,
(iii) measuring the activity of DNMT3A/ISGF3γ,
(iv) and selecting positively candidate compounds that blocks DNMT3A/ISGF3γ, blocks the action of DNMT3A/ISGF3γ or inhibits DNMT3A/ISGF3γ expression.

To identify a compound able to block the interaction between DNMT3A and ISGF3γ or inhibits DNMT3A/ISGF3γ expression, a test may be used. For example, a test using bioluminescence resonance energy transfer (BRET) system for assaying DNMT3A/ISGF3 interactions and identifying molecule having the ability to inhibit this interaction can be develop. For this purpose, cDNA of interDNMT3A and ISGF3g will be inserted in vectors designed for Bioluminescence Resonance Energy Transfer (BRET) experiments (pEYFP and phRluc, Invitrogen). Next, these vectors will be transfected in U251 cells (a GBM cell lines). Once the assay will be validated, BRET will be used for the screening of compounds libraries: a decrease of signal will interpreted as the highlighting of a molecule having the ability to inhibit the DNMT3A/ISGF3g interaction.

By "DNMT3A/ISGF3γ gene expression inhibitor" is meant a natural or synthetic compound which inhibits the expression of the DNMT3A gene expression or the ISGF3γ gene expression or both.

To identify such compound a test may be used. For example, to analyze the ability of a compound to inhibit the DNMT3A and ISGF3 expression, qPCR and ELISA experiments can be performed.

The invention also relates to i) compound according to the invention, and ii) a chemotherapeutic agent, as a combined preparation for simultaneous, separate or sequential for use in the treatment and prevention of cancer.

The invention also relates to i) compound according to the invention, and ii) a chemotherapeutic agent and iii) a radiotherapy or a radiotherapeutic agent, as a combined preparation for simultaneous, separate or sequential for use in the treatment and prevention of cancer.

As used herein, "radiotherapy" may consist of gamma-radiation, X-ray radiation, electrons or photons, external radiotherapy or curitherapy.

As used herein, the term "radiotherapeutic agent", is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

According to the invention, the chemotherapeutic agent may be the temozolomide, 5-aza-2'-deoxycytidine, Theaflavin 3, 3'-digallate, zebularine, decitabine, 4-amino-N-(4-aminophenyl), benzamide analogues of quinoline-based SGI-1027 (PMID: 24678024 or 23294304.

In one embodiment, the cancer according to the invention is a glioblastoma.

In one embodiment, the invention relates to i) compound according to the invention, and ii) a chemotherapeutic agent and iii) a radiotherapy, as a combined preparation for simultaneous, separate or sequential for use in the treatment and prevention of glioblastoma.

In a particular embodiment, the invention relates to i) compound according to the invention, and ii) the temozolomide and iii) a radiotherapy, as a combined preparation for simultaneous, separate or sequential for use in the treatment and prevention of glioblastoma.

Typically, the compound according to the invention includes but is not limited to a small organic molecule, an antibody, an intra-antibody, a nanobody and a polypeptide.

In one embodiment, the compound according to the invention may be a low molecular weight compound, e. g. a small organic molecule (natural or not).

The term "small organic molecule" refers to a molecule (natural or not) of a size comparable to those organic molecules generally used in pharmaceuticals. The term excludes biological macromolecules (e. g., proteins, nucleic acids, etc.). particular small organic molecules range in size up to about 10000 Da, more particularly up to 5000 Da, more particularly up to 2000 Da and most particularly up to about 1000 Da.

In one embodiment, the compound according to the invention is an antibody, an intra-antibody or a nanobody. Antibodies, intra-antibodies or nanobodies directed against DNMT3A or ISGF3γ proteins can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal or monoclonal antibodies. Monoclonal antibodies against DNMT3A or ISGF3γ proteins can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-DNMT3A or anti-ISGF3γ proteins single chain antibodies. Compounds useful in practicing the present invention also include anti-DNMT3A or anti-ISGF3γ antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to DNMT3A or ISGF3γ proteins.

Humanized anti-DNMT3A or anti-ISGF3γ antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816, 397).

Then, for this invention, neutralizing antibodies of DNMT3A or ISGF3γ are selected.

In one embodiment, the compound according to the invention is an anti-DNMT3A antibody.

In a particular embodiment, the antibody according to the invention may be the ab23565 antibody bought by Abcam or the H-295 antibody bought by Santa Cruz.

In another embodiment, the compound according to the invention is an anti-ISGF3γ antibody.

In one embodiment, the compound according to the invention is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then, for this invention, neutralizing aptamers of DNMT3A or ISGF3γ are selected.

In one embodiment, the compound according to the invention is a peptide, a polypeptide or a protein.

In a particular embodiment the peptide, the polypeptide or the protein can be a functional equivalent of DNMT3A or ISGF3γ. As used herein, a "functional equivalent" of DNMT3A or ISGF3γ is a compound which is capable of binding to DNMT3A or ISGF3γ. The term "functional equivalent" or "function-conservative variants" include fragments, mutants, and muteins of DNMT3A or ISGF3γ. The term "functionally equivalent" thus includes any equivalent of DNMT3A or ISGF3γ obtained by altering the amino acid sequence, for example by one or more amino acid deletions, substitutions or additions. Amino acid substitutions may be made, for example, by point mutation of the DNA encoding the amino acid sequence.

The functional equivalents include soluble forms of DNMT3A or ISGF3γ. A suitable soluble form of these proteins, or functional equivalents thereof, might comprise, for example, a truncated form of the protein from which the transmembrane domain has been removed by chemical, proteolytic or recombinant methods.

Particularly, the functional equivalent is at least 80% homologous to the corresponding protein. In a particular embodiment, the functional equivalent is at least 90% homologous as assessed by any conventional analysis algorithm such as for example, the Pileup sequence analysis software (Program Manual for the Wisconsin Package, 1996).

The term "a functionally equivalent fragment" as used herein also may mean any fragment or assembly of fragments of DNMT3A or ISGF3γ.

Functionally equivalent fragments may belong to the same protein family as the DNMT3A or ISGF3γ identified herein. By "protein family" is meant a group of proteins that share a common function and exhibit common sequence homology. Homologous proteins may be derived from non-human species. Particularly, the homology between functionally equivalent protein sequences is at least 25% across the whole of amino acid sequence of the complete protein. More particularly, the homology is at least 50%, even more particularly 75% across the whole of amino acid sequence of the protein or protein fragment. More particularly, homology is greater than 80% across the whole of the sequence. More particularly, homology is greater than 90% across the whole of the sequence. More particularly, homology is greater than 95% across the whole of the sequence.

The polypeptides of the invention may be produced by any suitable means, as will be apparent to those of skill in the art. In order to produce sufficient amounts of peptide, polypeptide or protein according to the invention or functional equivalents thereof for use in accordance with the present invention, expression may conveniently be achieved by culturing under appropriate conditions recombinant host cells containing the polypeptide of the invention. Particularly, the polypeptide is produced by recombinant means, by expression from an encoding nucleic acid molecule. Systems for cloning and expression of a polypeptide in a variety of different host cells are well known.

When expressed in recombinant form, the polypeptide may be generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also hosts for the production of recombinant protein, due to the ease with which bacteria may be manipulated and grown. A common bacterial host is *E. coli*.

In specific embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

In one embodiment, the peptide of the invention is the peptide P1 (SEQ ID NO:1).

Thus, the invention also relates to a peptide comprising the amino acids sequence: RPMPRLTFQAGDPYYI (SEQ ID NO:1) or a function-conservative variant thereof.

Thus, the peptide comprising the amino acids sequence SEQ ID NO: 1 or a function-conservative variant may be used for treating or preventing cancer.

Thus according to a particular embodiment, the invention relates to i) a compound which is the peptide P1 (SEQ ID NO:1) or a function-conservative variant thereof, and ii) the temozolomide, as a combined preparation for simultaneous, separate or sequential for use in the treatment and prevention of cancer.

Thus according to a particular embodiment, the invention relates to i) a compound which is the peptide P1 (SEQ ID NO:1) or a function-conservative variant thereof, and ii) the temozolomide, as a combined preparation for simultaneous, separate or sequential for use in the treatment and prevention of glioblastoma.

Thus according to a particular embodiment, the invention relates to i) a compound which is the peptide P1 (SEQ ID NO:1), and ii) the temozolomide and iii) a radiotherapy, as a combined preparation for simultaneous, separate or sequential for use in the treatment and prevention of cancer.

Thus according to a particular embodiment, the invention relates to i) a compound which is the peptide P1 (SEQ ID NO:1), and ii) the temozolomide and iii) a radiotherapy, as a combined preparation for simultaneous, separate or sequential for use in the treatment and prevention of glioblastoma.

In one embodiment, the compound is a functionally equivalent fragment of the peptide P1.

In one embodiment, the peptide P1 of SEQ ID NO:1 is used to sensitive cancer cell to a chemotherapeutic agent and particularly to temozolomide.

```
P1:    SEQ ID NO: 1:      RPMPRLTFQAGDPYYI

P1mut: SEQ ID NO: 2:      RPMPRLTAQAGAPYYI
```

In a particular embodiment, the invention relates to a peptide comprising the amino acids sequence SEQ ID NO:1 or a function-conservative variant thereof.

The invention also encompasses peptides that are function-conservative variants of the peptide comprising SEQ ID NO: 1 as described here above.

In one embodiment, the peptide according to the invention may differ from 1, 2 or 3 amino acids to the SEQ ID NO:1.

In another embodiment, the peptide according to the invention may differ from 4 or 5 amino acids to the SEQ ID NO:1.

In one embodiment, the peptide of the invention comprises at least 75% identity over said the SEQ ID NO: 1, even more preferably at least 80%, at least 85%, at least 90%, at least 95%, at least 97% and is still able to decrease tumor cell proliferation or still able to induce PCD in tumor cell.

In one embodiment, the peptide of the invention consists in the amino acid sequence as set forth in SEQ ID NO:1 or a variant thereof comprising at least 75%, preferably at least 80%, 85%, 90%, 95%, 96%, 97%, 98%, 99%, 99.5% or 99.9% identity with SEQ ID NO:1 and is still able for disrupting the DNMT3A/ISGF3γ interaction.

To verify whether the newly generated peptides induce a disruption of the DNMT3A/ISGF3γ interaction, a test as described above can be performed.

In one embodiment of the invention, said peptide is an amino acid sequence of less than 50 amino acids long that comprises the amino acid sequence SEQ ID NO:1 as defined here above.

In another embodiment of the invention, said soluble peptide is an amino acid sequence of less than 45 amino acids long that comprises the amino acid sequence SEQ ID NO:1 as defined here above.

In another embodiment of the invention, said soluble peptide is an amino acid sequence of less than 40 amino acids long that comprises the amino acid sequence SEQ ID NO:1 as defined here above.

In another embodiment of the invention, said soluble peptide is an amino acid sequence of less than 30 amino acids long that comprises the amino acid sequence SEQ ID NO:1 as defined here above.

In another embodiment of the invention, said soluble peptide is an amino acid sequence of less than 20 amino acids long that comprises the amino acid sequence SEQ ID NO:1 as defined here above.

In another embodiment of the invention, said soluble peptide is an amino acid sequence of less than 15 amino acids long that comprises the amino acid sequence SEQ ID NO:1 as defined here above.

In some embodiments the peptide, the polypeptide or the protein of the invention and particularly the peptide P1 is linked with at least one cell penetrating peptide (CPP).

The terms "cell penetrating peptide" or "CPP" are used interchangeably and refer to cationic cell penetrating peptides, also called transport peptides, carrier peptides, or peptide transduction domains. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refer to a peptide which, when brought into contact with a cell under appropriate conditions, passes from the external environment in the intracellular environment, including the cytoplasm, organelles such as mitochondria, or the nucleus of the cell, in conditions significantly greater than passive diffusion. Such penetrating peptides may be those described in Fonseca S. B. et al., Advanced Drug Delivery Reviews, 2009, 61: 953-964, Johansson et al., Methods in Molecular Biology, 2011, Vol. 683, Chapter 17, Bechara and Sagan, (2013) FEBS letters 587, 1693-1702.; Jones and Sayers (2012), Journal of controlled release: official journal of the Controlled Release Society 161, 582-591; Khafagy el and Morishita, (2012) Advanced drug delivery reviews 64, 531-539; Malhi and Murthy, (2012) Expert opinion on drug delivery 9, 909-935, in WO2004/011595 and in WO2003/011898. All that CPP are incorporated by reference.

In a particular embodiment, the cell penetrating peptide comprises or consists of: Tat peptide, polyarginines peptide, HA2-R9 peptide, Penetratin peptide, Transportan peptide, Vectocell® peptide, maurocalcine peptide, decalysine peptide, HIV-Tat derived PTD4 peptide, Hepatitis B virus Translocation Motif (PTM) peptide, mPrP1-28 peptide, POD, pVEC, EB1, Rath, CADY, Histatin 5, Antp peptide, Cyt86-101 peptide, DPT peptide.

In another particular embodiment, the peptide, the polypeptide or the protein of the invention is linked to two, three or more penetrating peptides.

In another embodiment, the compound according to the invention is an inhibitor of DNMT3A or ISGF3γ gene expression.

Small inhibitory RNAs (siRNAs) can also function as inhibitors of DNMT3A or ISGF3γ expression for use in the present invention.

DNMT3A or ISGF3γ gene expression can be reduced by contacting a subject or cell with a small double stranded RNA (dsRNA), or a vector or construct causing the production of a small double stranded RNA, such that DNMT3A or ISGF3γ gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

In one embodiment, miRNA can be used to as inhibitors of DNMT3A or ISGF3γ gene expression. For example, miRNA-29a and b, miRNA-143, miRNA-101 and miRNA 369 can be used to inhibit DNMT3A gene expression and miRNA-106 can be used to inhibit ISGF3G gene expression.

Ribozymes can also function as inhibitors of DNMT3A or ISGF3γ gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of DNMT3A or ISGF3γ mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of DNMT3A or ISGF3γ gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and particularly cells expressing DNMT3A or ISGF3γ. Particularly, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a particular type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Particular viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Particular viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a particular embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, e.g., a viral promoter, such as CMV promoter or any synthetic promoters.

Another object of the invention relates to a method for treating and preventing cancer comprising administrating to a subject in need thereof a therapeutically effective amount of a compound which is a DNMT3A/ISGF3γ antagonist or a compound which is a DNMT3A/ISGF3γ gene expression inhibitor.

In one embodiment, the invention relates to a method for treating and preventing glioblastoma comprising administrating to a subject in need thereof a therapeutically effective amount of a compound which is a DNMT3A/ISGF3γ antagonist or a compound which is a DNMT3A/ISGF3γ gene expression inhibitor.

Therapeutic Composition

Another object of the invention relates to a therapeutic composition comprising a compound according to the invention for use in the treatment and prevention of cancer.

In one embodiment, the invention relates to a therapeutic composition comprising a compound according to the invention for use in the treatment and prevention of glioblastoma Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Particularly, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Pharmaceutical compositions of the present invention may comprise a further therapeutic active agent. The present invention also relates to a kit comprising a compound according to the invention and a further therapeutic active agent.

In one embodiment said therapeutic active agent may be an anti-cancer agent.

The invention will be further illustrated by the following figures and examples. However, these examples and figures should not be interpreted in any way as limiting the scope of the present invention.

Figure 1:
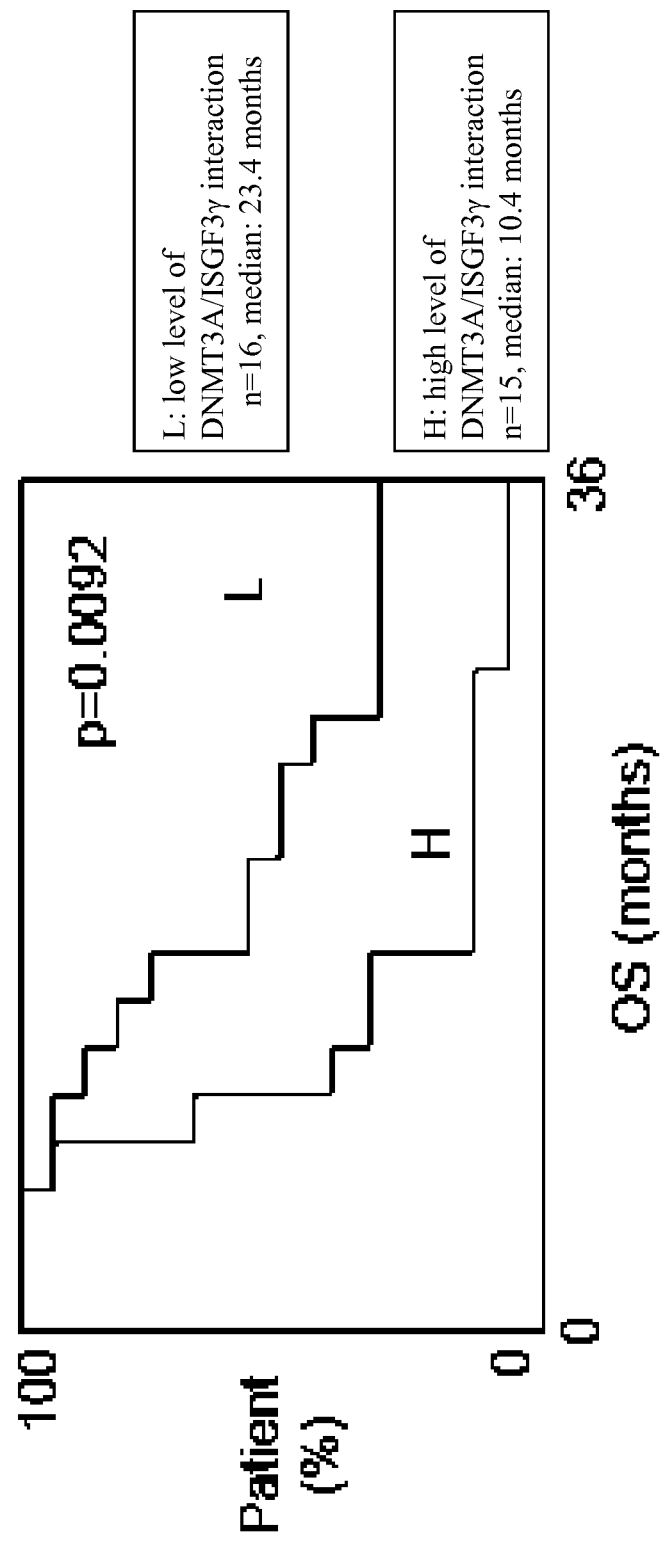
FIG. 1. A high level of DNMT3A/ISGF3γ interaction is a poor prognosis factor.

Kaplan-Meier curves illustrate the difference of overall survival (OS) between patient with high (H) and low (L) levels of DNMT3A/ISGF3γ interaction. p value is obtained by performing a Cox Proportional Hazards Survival Regression test.

FIG. 2. Specific disruption of DNMT3a/ISGF3γ interaction.

A and B. Impact of peptides miming the DNMT3A/ISGF3γ binding regions on the DNMT3A/ISGF3γ interaction. Pictures and graphs are representatives of three independent pull-down experiments. I: input. p values were obtained by performing a t test.

FIG. 3. Effect of a treatment associating the P1 peptide with TMZ in a swiss nude mice model of established tumors.

A. Design of the experiment. Tumor establishment indicates that 2.106 PCTC-GBM were injected to form a tumor of which the volume was equal to 100 mm3±33.3. Then, mice were treated with indicated treatment. D: day, w: week, it: intra-tumoral, ip: Intraperitoneal.

B. Graph illustrates the impact of the 4 considered treatments on tumor weight of established tumors. Open circles represent mice. Black circles represent the average±standard deviation obtained for each treatment. p values were obtained by performing a t test.

Example

Material & Methods

Patient Characteristics.

Overall survival was measured from the date of surgical resection to the death. In each tumor grade, all patients included in this study had similar management and similar treatment (including temozolomide (TMZ) for GBM). Patient material as well as records (diagnosis, age, sex, date of death, Karnofsky performance score (KPS)) was used with confidentiality according to French laws and recommendations of the French National Committee of Ethic.

Primary Cultured Tumor Cells (PCTC).

Fresh brain tumor tissues obtained from the neurosurgery service of the Laennec Hospital (Nantes/Saint-Herblain, France) were collected and processed within 30 min after resection. The clinical protocol was approved by the French laws of ethics with informed consent obtained from all subjects. The primary cultured tumor cells were obtained after mechanical dissociation according to the technique previously described. Briefly, tumor tissue was cut into pieces of 1-5 mm3 and plated in a 60 mm2 tissue culture dish with DMEM with 10% FBS and antibiotics. Additionally and in parallel, minced pieces of tumor were incubated with 200 U/ml collagenase I (Sigma, France) and 500 U/ml DNaseI (Sigma, France) in PBS during 1 hr at 37° C. with vigorous constant agitation. The single-cell suspension was filtered through a 70 mm cell strainer (BD Falcon, France), washed with PBS, and suspended in DMEM-10% FBS. Cell cultures were subsequently split 1:2 when confluent and experiments were done before passage 3-5.

Proximity Ligation In Situ Assay (P-LISA).

Cells were cultured for 24 h on cover slip. Cells were then fixed with 4% paraformaldehyde in PBS pH7.4 for 15 min at room temperature. Permeabilization is performed with PBS containing 0.5% Triton X-100 for 20 min at room temperature. Blocking, staining, hybridization, ligation, amplification and detection steps were realized according to manufacturer's instructions (Olink Bioscience, Sweden). All incubations were performed in a humidity chamber. Amplification and detection steps were performed in dark room. Fluorescence was visualized by using the Axiovert 200M microscopy system (Zeiss, Le Pecq, France) with ApoTome module (X63 and numerial aperture 1.4). Preparations were mounted by using ProLong Gold antifade reagent with DAPI (Life Technologies, France). Pictures acquisition was realized in structured illumination microscopy. After decovolving (3.5 Huygens Essential software (SVI)), 3D view was obtained by using Amira.4.1.1 program. Finally, the images were analyzed by using the freeware "BlobFinder" available for download from www.cb.uu.se/~amin/BlobFinder. Thus, we obtained either number of signals per nuclei since nuclei can be automatically identified.

Epitope Mapping.

Peptides were spotted on an Amino-PEG500-UC540 membrane using a MultiPep peptide synthesizer (Intavis AG, Cologne, Germany) at a loading capacity of 400 nmol/cm2. After synthesis the membrane was dried then the capped side-chains were deprotected by cleavage for 1 h with a cocktail containing 95% trifluoroacetic acid, 3% tri-isopropyl, 2% H2O. The trifluoroacetic acid was removed and the membrane rinsed with dichloromethane, followed by dimethylformaldehyde and then ethanol. The membrane was saturated before incubation with the considered recombinant protein for 2 h at room temperature. After which, it was washed three times, positive peptides were revealed using antibodies coupled to a fluorochrome. Typhoon (GE Healthcare, France) was used to determine fluorescence. The binding intensities of the considered recombinant protein for the spotted peptides were determined by quantification using ImageJ software and converted to sequence-specific normalized units. The intensities obtained for each peptide covering a given amino acid were added and divided by the number of peptides.

Pull-Down Assay.

Pull-down assays were performed by using the GST/His Tagged-Protein Interaction Pull-Down Kits (Thermo Scientific, France). Briefly, 100 μg of bait protein were immobilized on column via an incubation at 4° C. for 1 h with gentle mixing. After washing, 1 μg of prey protein was added for 1 h at 4° C. with gentle rocking motion on a rotating platform. After washes and elution, the "bait-prey" interaction was analyzed by SDS-PAGE and Western blot methods. Competitive pull-down experimentations were realized by pre-incubating considered peptides for 1 h at 37° C.

Western Blot Analysis.

In brief, proteins were size fractionated by sodium dodecyl sulfate-polyacrylamide gel electrophoresis. Proteins were transferred onto nitrocellulose or PVDF membrane. Saturation and blotting were realized by using SNAP i.™ Protein Detection System (Millipore, France). The detection of proteins was performed using ECL™ (Amersham Biosciences, France) and/or SuperSignal west femto Maximum Sensitivity (Thermo Scientific, France) chemilumenscence reagents. The detection of proteins was performed using the FusionX7 Imager (Fisher Scientific, France).

Transfer of Peptides into Cells Via Electroporation.

For electroporation, NLS sequence was added to peptides. Cells were harvested during the exponential growth phase by trypsinization and were resuspended in their original media. They were washed in PBS, pH 7.2 (0.14 M NaCl, 2 mM KCl, 8 mM Na2HPO4 and 1.5 mM NaH2PO4) and resuspended at a concentration of 0.6×106 cells/ml in original culture medium. Next, 0.8 ml of the cell suspension was mixed with the peptides (50 μg/ml), allowed to stand at room temperature for 10 min and added to a disposable 0.4 cm Bio-Rad electroporation cuvette (Bio-Rad, France). An equivalent volume of DMSO was added to a cell suspension without peptide for use as a control (also named untreated). Electroporation efficiency for each cell line was initially determined by flow cytometry by uptake of the fluorescent dye, lucifer yellow (Sigma, France). Electroporation was carried out in a Gene-Pulser (Bio-Rad, France) with cells exposed to one pulse. The following parameters were used: cuvette gap 0.4 cm, voltage 0.3 kV, time constant 35 ms, and capacitor 960 μF. Following electroporation, cells were allowed to recover by standing at room temperature for 10 min, then removed from the electroporation chamber, washed twice in PBS and resuspended in 2 ml of original culture medium.

Measure of Global DNA Methylation.

DNA was extracted by using the QiaAmp DNA mini Kit (Qiagen, France). Next, global DNA methylation was estimated by quantifying the presence of 5-methylcytosine using Methylamp Global DNA methylation Quantification kit (Euromedex-Epigentek, France) according to the manufacturers's instructions.

Measure of Cell Death.

Percentages of cell death were evaluated by using a Trypan Blue Stain 0.4%, and the Countess® Automated Cell Counter (Life Technologies, France). Cell death was induced using temozolomide (25 μM) and irradtiation (2 Gy) such as previously described.

Proliferation Assay and Doubling Time.

Doubling time (i.e. the period of time required for a quantity to double in size) was calculated by using the Doubling Time Online Calculator website (Roth V. 2006, http://www.doubling-time.com/compute.php) and counting the proliferation of 103 cells over 120 hours. Cell number was determined, every 24 h over 120 h, using the Countess® Automated Cell Counter (Life Technologies, France).

Migration Assay—Scratch Test.

Cell migration assay was performed using a scratch technique. Cells were plated in 6-well plates at 80-90%, and were treated with 10 µg/ml mitomycin C (Sigma, Farnce) for 2 hours (in order to remove the influence of cell proliferation). Cells were then scratched. Cell migration was monitored by microscopy. The images acquired for each sample were analyzed quantitatively. For each image, distances between one side of scratch and the other were measured. By comparing the images from time 0 to the last time point (24 hours), we obtain the distance of each scratch closure on the basis of the distances that are measured.

Invasion Assay.

All of the procedures were followed according to the manufacturer's instructions (QCM 24-Well Collagen-Based Cell Invasion Assay, Millipore, France). In brief, 200 µl serum-free medium containing 2×105 cells were seeded into the invasion chamber and placed into the 24 well plate containing 500 µl complete medium. After 72 h incubation at 37° C., media was removed from the chamber, and cells were stained by putting the chamber in staining solution for 20 min at room temperature. Non-invaded cells were carefully removed from the top-side of the chamber. Stained chamber was inserted into a clean well containing 200 µl of extraction buffer for 15 min at room temperature. 100 µl extracted stained solution from the chamber was transferred into the 96 well plate and optical density was measured at 560 nm with a spectrophotometer.

Tumorigenicity Assay.

Cultured cells were harvested by trypsinization, washed and resuspended in saline buffer. Cell suspensions were injected s.c. as 2.106 cells in 0.05 ml of PBS with equal volume of matrigel matrix (Becton Dickinson, France) in the flank of 7/8-week-old Nude NMRI-nu female mice (Janvier, France). After tumor establishment, mice were treated with temozolomide and/or peptides via intra-tumor injection (it). To obtain tumor weigh, each tumor was surgically removed and is weighed. All experimental procedures using animals were realized in accordance with the guidelines of Institutional Animal Care and the French National Committee of Ethics.

Statistical Analysis.

All experiments were done at least in triplicates. Significance of the differences in means was calculated using Student-t test. Survival curves were plotted according to Kaplan-Meier method and compared by the Cox proportional hazards survival regression analysis (such as indicated on the corresponding figures). Significance of correlation between two parameters was calculated using Pearson's test.

Results

A High Level of DNMT3A/ISGF3γ Interaction Correlates with a Poor Level of Sensitivity to Temozolomide/Irradiation-Induced Cell Death.

To determine whether the presence of interaction between DNMT3A and a DNMT3A-binding protein (D3ABP) could permit to identify a subpopulation of GBM patients whose the glioma cells harbor a phenotype of resistance to the temozolomide/irradiation treatment, we have established 31 primary cultured tumor cells (PCTCs) from patient-derived biopsies. Then, these PCTC were used to evaluate the putative correlation between the number of certain DNMT3A/D3A-BP interactions and the temozolomide/irradiation-induced (TMZ/IR-induced) cell death percentage (data not shown). In our study, we focused on the DNMT3A/HDAC1, DNMT3A/AP2α, DNMT3A/GATA1 and DNMT3A/ISGF3γ interaction since we and other have already demonstrated their existence [Fuks F et al., 2001 and Hervouet E et al., 2009]. Proximity Ligation In Situ Assay (P-LISA) was used to monitor the interaction of interest. The TMZ/IR-induced cell death percentage was estimated by using trypan blue method (data not shown). The number of DNMT3A/D3A-BP interactions of interest and the TMZ/IR-induced cell death percentage were plotted against each other (data not shown). Statistical analysis using Pearson's correlation test showed a significant and inverse correlation only between the number of DNMT3A/ISGF3γ interactions and the TMZ/IR-induced cell death percentage (p=0.002) (data not shown). These results suggested that DNMT3A/ISGF3γ could play a crucial role in the poor response prognosis of glioma cells to the TMZ/IR treatment.

A High Level of DNMT3A/ISGF3γ Interaction is a Poor Prognosis Factor.

The 31 patients were divided into two groups based on the DNMT3A/ISGF3γ interaction levels found on their tumor biopsies. Tumors from 15 patients expressed high levels of DNMT3A/ISGF3γ interaction (higher than the median of DNMT3A/ISGF3γ interaction, 12.5), while 16 patients had a DNMT3A/ISGF3γ interaction equal to or lower than 12.5. Overall survival curves were estimated by the Kaplan-Meier method and compared with the Cox Proportional Hazards Survival Regression Analysis (FIG. 1). A significant difference was observed in overall survival (p=0.0092) between patients whose tumors had high levels of DNMT3A/ISGF3γ interaction and those whose tumors did not. These data indicate that a high level of DNMT3A/ISGF3γ interaction is a poor prognosis factor.

Specific Disruption of DNMT3A/ISGF3γ Interaction.

The double fact that high level of DNMT3a/ISGF3γ interaction was associated with a poor response prognosis to the temozolomide/irradiation treatment and was associated with of poor prognosis of overall survival, suggest that DNMT3A/ISGF3γ interaction could be used as a therapeutic target.

To develop a therapeutic strategy aiming to inhibit the DNMT3A/ISGF3γ interaction, we performed a set of experiments aiming to characterize the DNMT3A/ISGF3γ interaction. In this set of experiments, epitope mapping analysis was performed to identify the amino acids region of DNMT3A interaction with ISGF3γ. Thus, the primary sequence of DNMT3A was decomposed into 12-mer peptides overlapping by 10 residues covalently bound to a nitrocellulose membrane. Two negative controls were performed to observe that neither the incubation of GST protein (2 µg) nor the use of antibodies against ISGF3γ induced the detection of positive peptides (data not shown). Then, 2 µg of GST-ISGF3γ protein were incubated with the membrane. The positive peptides for an interaction with GST-ISGF3γ were then detected by using Thyphoon and antibodies directed against ISGF3γ (data not shown). After fluorescence quantification, the sequences of amino acids of DNMT3A interacting with GST-ISGF3γ were determined (data not shown). Thus, we observed that the sequences 85-99, 103-129, 178-207, 235-246, 256-273, 331-360, 409-433 and 547-574 of the DNMT3A protein sequence were implicated in the DNMT3A/ISGF3γ interaction.

To validate the implication of these amino acid domains on the DNMT3A/ISGF3γ interaction, we derived peptides from these domains in order to test the ability of these peptides to inhibit the DNMT3A/ISGF3γ interaction in a pull-down assay (data not shown). We thus noted that only P1 (RPMPRLTFQAGDPYYI, SEQ ID NO:1) inhibited the DNMT3A/ISGF3γ interaction (FIG. 2A). The efficiency of P1 to inhibit the DNMT3A/ISGF3γ interaction was also reinforced by the fact that 1) a mutated P1 peptide (P1$^{mut}$, RPMPRLTAQAGAPYYI, SEQ ID NO:2) does not inhibit the DNMT3A/ISGF3γ interaction (FIG. 2A) and 2) DNMT3A/ISGF3γ interaction decreased in presence of increasing concentration of P1 peptide (FIG. 2B).

Proximity Ligation In Situ Assays (P-LISA) were next used to monitor the DNMT3A/ISGF3γ interactions in cells. For these experiments, we used a PCTC (named PCTC #1). Electroporation was used to transfect P1 in cells. P-LISA were performed 12 hr after electroporation. Thus, we noted that red dots representing the DNMT3A/ISGF3γ interactions decreased when cells were treated with the P1 and not in presence of P1$^{mut}$ (data not shown).

All these results indicated that P1 peptide induced the disruption of DNMT3A/ISGF3γ interactions.

Specific Effect of P1 Peptide.

P1 was designed to inhibit the DNMT3A/ISGF3γ interactions. However, P1 could also affect other interaction existing between DNMT3 and a D3A-BP. To investigate this point, we analyzed the effect of P1 on the DNMT3A/D3A-BP interactions of interest. We noted that P1 has no effect on the integrity of the DNMT3A/GATA1, DNMT3A/AP2γ and DNMT3A/HDAC1 interactions in PCTC #1.

The analysis of all interactions being impossible, we postulated that if P1 inhibited a large number of DNMT3A/D3A-BP interactions, an hypomethylation phenotype would be observable. To observe the putative P1-induced DNA hypomethylation, PCTC #1 were treated during 30 days with P1 (data not shown). Other DNMT inhibitors (5-aza-2-deoxycytidine (5-aza), theaflavin 3,3 digallate (a DNMT3A inhibitor, hereafter called TFD), or peptides (UP peptide, a peptide inhibiting the DNMT1/PCNA/UHRF1 interactions)) were also used as control conditions. ELISA monitoring the global level of 5-methylcytosine revealed that P1 had not effect on the global level of 5-methylcytosine, while the 5-aza, TFD and UP treatments decreased the global level of DNA methylation (data not shown).

Based on these data, we conclude that P1 seems to be specific for disrupting the DNMT3A/ISGF3γ interaction and without promoting global DNA hypomethylation.

Impact of P1 Peptide on Cancer Hallmarks/Phenotypes.

We then determined the impact of the P1-induced disruption of the DNMT3A/ISGF3γ interactions on several cancer hallmarks/phenotypes including proliferation level, invasion, migration and evasion of apoptosis (or more particularly the sensitivity of apoptosis induced by a therapeutic treatment). For this purpose, cells were treated by P1 and TDF such as previously described.

To evaluate the impact of the P1-induced disruption of the DNMT3A/ISGF3γ interactions on the sensitivity of apoptosis induced by a therapeutic treatment, we measured the percentage of temozolomide+irradiation-induced cell death since temozolomide (TMZ) and irradiation are conjugated in anti-GBM treatment [Cheray M et al., 2013 and Louis D et al., 2007]. Results show that the percentage of cell death of P1 and TDF treated cells increased, and the percentage of cell death of P1 treated cells was higher than the one obtained with TDF. Thus, we conclude that P1 acts as a sensitizer of the temozolomide+irradiation-induced cell death.

To estimate the impact of the P1-induced disruption of DNMT3A/ISGF3γ interactions on proliferation, we calculated the doubling time. We found that both P1 and TFD treatments have no effect on the doubling time of cells (data not shown).

Impact of the P1-induced disruption of the DNMT3A/ISGF3γ interactions on migration capability was next estimated by performing a scratch test assay. Results indicate that P1 treatment decreased cell migration while TFD treatments had no effect on cell migration.

Impact of the P1 and TFD treatments on cell invasion was next estimated by performing a collagen-based cell invasion assay. results indicate that P1 unmodified the cell invasion characteristic, while TDF treatment promoted the cell invasion.

To summarize these data, we created and calculated the Score of Modulation of Cancer Hallmarks (SMoCH) by attributing −1 when the peptide/treatment enhanced a cancer hallmark, 0 when peptide/treatment did not modify a cancer hallmark and +1 when the peptide/treatment inhibited a cancer hallmark. Thus, a positive SMoCH suggests that the considered peptide/treatment inhibits more cancer hallmarks than it promotes them, so the benefit/risk balance is favorable for using the considered peptide/treatment in anticancer therapy. Results indicating that P1 treatment is in this situation, we concluded that P1 treatment could be efficient in anti-cancer therapy.

Effect of a Treatment Associating P1 Peptide with TMZ in a Swiss Nude Mice Model of Established Tumors.

Standard anti-GBM treatment using temozolomide as chemotherapeutic agent, we next investigated the effect of a treatment associating P1 peptide with TMZ in a swiss nude mice model of established tumors. For this purpose, 16 swiss Nude mice were injected subcutaneously by $2.10^6$ glioma cells (having high level of DNMT3A/ISGF3γ interactions (FIG. 3A). Next, when the tumor volume was equal to 100 mm$^3$, 4 mice were randomly untreated, treated with TMZ, TMZ+P1, TMZ+P1$^{mut}$ or P1 (called T1 and T5 respectively). After 3 weeks of treatment, we noted that TMZ treatment was inefficient to limit tumor growth since no statistical difference was observed between untreated mice and mice treated with TMZ only, and between untrated mice and mice treated with P1 (FIG. 3B). More interestingly, we noted that the TMZ+P1 treatment reduced tumors volumes, while the TMZ+P1' treatment is inefficient to reduce tumor growth. Thus, our data indicated that the use of P1 with TMZ promoted the TMZ-induced reduction of tumor growth.

The use of P1 peptide does not promote global DNA hypomethylation and MGMT demethylation.

In glioma, MGMT methylation is associated with a good responsive of anti-glioma treatment including TMZ and irradiation [Esteller M et al., 2000 and Hegi M et al., 2005]. Thus, we have analyzed whether the use of P1 could modulate the methylation level of MGMT. qMSP experiment indicated that the methylation level of MGMT remains unchanged when cells were treated with P1 (data not shown)

REFERENCES

Throughout this application, various references describe the state of the art to which this invention pertains. The disclosures of these references are hereby incorporated by reference into the present disclosure.

Amato R, Stephenson J, Hotte S, Nemunaitis J, Belanger K, Reid G, et al. MG98, a second-generation DNMT1 inhibitor, in the treatment of advanced renal cell carcinoma. Cancer Invest. 2012; 30: 415-21.

Cheray M, Pacaud R, Nadaradjane A, Vallette F, Cartron P F. Specific inhibition of one DNMT1-including complex influences the tumor initiation and progression. Clinical Epigenetics. 2013; 5: 9.

Chik F, Szyf M. Effects of specific DNMT gene depletion on cancer cell transformation and breast cancer cell invasion; toward selective DNMT inhibitors. Carcinogenesis. 2011; 32: 224-32.

Esteller M, Garcia-Foncillas J, Andion E, Goodman S N, Hidalgo O F, Vanaclocha V, et al. Inactivation of the DNA-repair gene MGMT and the clinical response of gliomas to alkylating agents. N Engl J Med. 2000; 343: 1350-4.

Fuks F, Burgers W, Godin N, Kasai M, Kouzarides T. Dnmt3a binds deacetylases and is recruited by a sequence-specific repressor to silence transcription. EMBO J. 2001; 20: 2536-44.

Hegi M, Diserens A, Gorlia T, Hamou M, de Tribolet N, Weller M, et al. MGMT gene silencing and benefit from temozolomide in glioblastoma. N Engl J Med. 2005; 352: 991-1003.

Hervouet E, Vallette F M, Cartron P F. Dnmt3/transcription factor interactions as crucial players in targeted DNA methylation. Epigenetics. 2009; 4.

Kuck D, Singh N, Lyko F, Medina-Franco J. Novel and selective DNA methyltransferase inhibitors: Docking-based virtual screening and experimental evaluation. Bioorg Med Chem. 2010; 18: 822-9.

Kuck D, Caulfield T, Lyko F, Medina-Franco J. Nanaomycin A selectively inhibits DNMT3B and reactivates silenced tumor suppressor genes in human cancer cells. Mol Cancer Ther. 2010; 9: 3015-23.

Lee B, Yegnasubramanian S, Lin X, Nelson W. Procainamide is a specific inhibitor of DNA methyltransferase 1. J Biol Chem. 2005; 280: 40749-56.

Louis D, Ohgaki H, Wiestler O, Cavenee W, Burger P, Jouvet A, et al. The 2007 WHO classification of tumours of the central nervous system. Acta Neuropathol. 2007; 114: 97-109.

Medina-Franco J, Lopez-Vallejo F, Kuck D, Lyko F. Natural products as DNA methyltransferase inhibitors: a computer-aided discovery approach. Mol Divers. 2011; 15: 293-304.

Rajavelu A, Tulyasheva Z, Jaiswal R, Jeltsch A, Kuhnert N. The inhibition of the mammalian DNA methyltransferase 3a (Dnmt3a) by dietary black tea and coffee polyphenols. BMC Biochem. 2011; 21: 12-6.

Suzuki T, Tanaka R, Hamada S, Nakagawa H, Miyata N. Design, synthesis, inhibitory activity, and binding mode study of novel DNA methyltransferase 1 inhibitors. Bioorg Med Chem Lett 2010; 20: 1124-7.

Venza M, Visalli M, Catalano T, Fortunato C, Oteri R, Teti D, et al. Impact of DNA methyltransferases on the epigenetic regulation of tumor necrosis factor-related apoptosis-inducing ligand (TRAIL) receptor expression in malignant melanoma. Biochem Biophys Res Commun 2013; 441: 743-50.

Yoo J, Medina-Franco J. Inhibitors of DNA methyltransferases: insights from computational studies. Curr Med Chem. 2012; 19: 3475-87.

Yoo J, Kim J, Robertson K, Medina-Franco J. Molecular modeling of inhibitors of human DNA methyltransferase with a crystal structure: discovery of a novel DNMT1 inhibitor. Adv Protein Chem Struct Biol. 2012; 87: 219-47.

---

The invention claimed is:

1. A method of treating cancer comprising administering to a subject in need thereof a therapeutically effective amount of a DNMT3A/ISGF3γ antagonist which reduces the interaction between DNMT3A and ISGF3γ, wherein the antagonist is a peptide comprising the amino acid sequence: RPMPRLTFQAGDPYYI (SEQ ID NO:1), wherein the peptide is less than 50 amino acids in length, or a function-conservative variant thereof, wherein the function-conservative variant consists of a sequence that differs from SEQ ID NO:1 by 1, 2, 3, 4, or 5 amino acids, and administering to the subject a chemotherapeutic agent and/or a radiotherapy.

2. The method of claim 1, wherein the peptide or the function-conservative variant thereof is administered simultaneously, separately or sequentially with the chemotherapeutic agent and the radiotherapy.

3. The method of claim 1, wherein the chemotherapeutic agent is temozolomide and wherein temozolomide and a radiotherapy are administered simultaneously, separately or sequentially with the peptide or function-conservative variant thereof.

4. The method of claim 1, wherein the cancer is glioblastoma.

5. The method of claim 1, wherein the cancer is selected from the group consisting of bile duct cancer, bladder cancer, bone cancer, brain and central nervous system, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer.

* * * * *

SEQUENCE LISTING

```
<160> NUMBER OF SEQ ID NOS: 3

<210> SEQ ID NO 1
<211> LENGTH: 16
<212> TYPE: PRT
<213> ORGANISM: Artificial
<220> FEATURE:
<223> OTHER INFORMATION: Synthetic P1

<400> SEQUENCE: 1

Arg Pro Met Pro Arg Leu Thr Phe Gln Ala Gly Asp Pro Tyr Tyr Ile
1               5                   10                  15

<210> SEQ ID NO 2
<211> LENGTH: 16
<212> TYPE: PRT
<213> ORGANISM: Artificial
<220> FEATURE:
<223> OTHER INFORMATION: Synthetic P1mut

<400> SEQUENCE: 2

Arg Pro Met Pro Arg Leu Thr Ala Gln Ala Gly Ala Pro Tyr Tyr Ile
1               5                   10                  15

<210> SEQ ID NO 3
<211> LENGTH: 912
<212> TYPE: PRT
<213> ORGANISM: Homo sapiens

<400> SEQUENCE: 3
```

```
Met Pro Ala Met Pro Ser Ser Gly Pro Gly Asp Thr Ser Ser Ser Ala
1               5                   10                  15

Ala Glu Arg Glu Glu Asp Arg Lys Asp Gly Glu Gln Glu Glu Pro
            20                  25                  30

Arg Gly Lys Glu Glu Arg Gln Glu Pro Ser Thr Thr Ala Arg Lys Val
            35                  40                  45

Gly Arg Pro Gly Arg Lys Arg His Pro Pro Val Glu Ser Gly Asp
        50                  55                  60

Thr Pro Lys Asp Pro Ala Val Ile Ser Lys Ser Pro Ser Met Ala Gln
65                  70                  75                  80

Asp Ser Gly Ala Ser Glu Leu Leu Pro Asn Gly Asp Leu Glu Lys Arg
                85                  90                  95

Ser Glu Pro Gln Pro Glu Glu Gly Ser Pro Ala Gly Gly Gln Lys Gly
                100                 105                 110

Gly Ala Pro Ala Glu Gly Glu Gly Ala Ala Glu Thr Leu Pro Glu Ala
                115                 120                 125

Ser Arg Ala Val Glu Asn Gly Cys Cys Thr Pro Lys Glu Gly Arg Gly
    130                 135                 140

Ala Pro Ala Glu Ala Gly Lys Glu Gln Lys Glu Thr Asn Ile Glu Ser
145                 150                 155                 160

Met Lys Met Glu Gly Ser Arg Gly Arg Leu Arg Gly Leu Gly Trp
                165                 170                 175

Glu Ser Ser Leu Arg Gln Arg Pro Met Pro Arg Leu Thr Phe Gln Ala
                180                 185                 190

Gly Asp Pro Tyr Tyr Ile Ser Lys Arg Lys Arg Asp Glu Trp Leu Ala
                195                 200                 205

Arg Trp Lys Arg Glu Ala Glu Lys Lys Ala Lys Val Ile Ala Gly Met
    210                 215                 220

Asn Ala Val Glu Glu Asn Gln Gly Pro Gly Glu Ser Gln Lys Val Glu
225                 230                 235                 240

Glu Ala Ser Pro Pro Ala Val Gln Gln Pro Thr Asp Pro Ala Ser Pro
                245                 250                 255

Thr Val Ala Thr Thr Pro Glu Pro Val Gly Ser Asp Ala Gly Asp Lys
                260                 265                 270

Asn Ala Thr Lys Ala Gly Asp Asp Glu Pro Glu Tyr Glu Asp Gly Arg
                275                 280                 285

Gly Phe Gly Ile Gly Glu Leu Val Trp Gly Lys Leu Arg Gly Phe Ser
                290                 295                 300

Trp Trp Pro Gly Arg Ile Val Ser Trp Trp Met Thr Gly Arg Ser Arg
305                 310                 315                 320

Ala Ala Glu Gly Thr Arg Trp Val Met Trp Phe Gly Asp Gly Lys Phe
                325                 330                 335

Ser Val Val Cys Val Glu Lys Leu Met Pro Leu Ser Ser Phe Cys Ser
                340                 345                 350

Ala Phe His Gln Ala Thr Tyr Asn Lys Gln Pro Met Tyr Arg Lys Ala
                355                 360                 365

Ile Tyr Glu Val Leu Gln Val Ala Ser Ser Arg Ala Gly Lys Leu Phe
                370                 375                 380

Pro Val Cys His Asp Ser Asp Glu Ser Asp Thr Ala Lys Ala Val Glu
385                 390                 395                 400

Val Gln Asn Lys Pro Met Ile Glu Trp Ala Leu Gly Gly Phe Gln Pro
                405                 410                 415
```

```
Ser Gly Pro Lys Gly Leu Glu Pro Pro Glu Glu Lys Asn Pro Tyr
            420                 425                 430

Lys Glu Val Tyr Thr Asp Met Trp Val Glu Pro Glu Ala Ala Tyr
            435                 440                 445

Ala Pro Pro Pro Ala Lys Lys Pro Arg Lys Ser Thr Ala Glu Lys
450                 455                 460

Pro Lys Val Lys Glu Ile Ile Asp Glu Arg Thr Arg Glu Arg Leu Val
465                 470                 475                 480

Tyr Glu Val Arg Gln Lys Cys Arg Asn Ile Glu Asp Ile Cys Ile Ser
                485                 490                 495

Cys Gly Ser Leu Asn Val Thr Leu Glu His Pro Leu Phe Val Gly Gly
            500                 505                 510

Met Cys Gln Asn Cys Lys Asn Cys Phe Leu Glu Cys Ala Tyr Gln Tyr
            515                 520                 525

Asp Asp Asp Gly Tyr Gln Ser Tyr Cys Thr Ile Cys Cys Gly Gly Arg
            530                 535                 540

Glu Val Leu Met Cys Gly Asn Asn Cys Cys Arg Cys Phe Cys Val
545                 550                 555                 560

Glu Cys Val Asp Leu Leu Val Gly Pro Gly Ala Ala Gln Ala Ala Ile
                565                 570                 575

Lys Glu Asp Pro Trp Asn Cys Tyr Met Cys Gly His Lys Gly Thr Tyr
            580                 585                 590

Gly Leu Leu Arg Arg Arg Glu Asp Trp Pro Ser Arg Leu Gln Met Phe
            595                 600                 605

Phe Ala Asn Asn His Asp Gln Glu Phe Asp Pro Pro Lys Val Tyr Pro
610                 615                 620

Pro Val Pro Ala Glu Lys Arg Lys Pro Ile Arg Val Leu Ser Leu Phe
625                 630                 635                 640

Asp Gly Ile Ala Thr Gly Leu Leu Val Leu Lys Asp Leu Gly Ile Gln
                645                 650                 655

Val Asp Arg Tyr Ile Ala Ser Glu Val Cys Glu Asp Ser Ile Thr Val
            660                 665                 670

Gly Met Val Arg His Gln Gly Lys Ile Met Tyr Val Gly Asp Val Arg
            675                 680                 685

Ser Val Thr Gln Lys His Ile Gln Glu Trp Gly Pro Phe Asp Leu Val
            690                 695                 700

Ile Gly Gly Ser Pro Cys Asn Asp Leu Ser Ile Val Asn Pro Ala Arg
705                 710                 715                 720

Lys Gly Leu Tyr Glu Gly Thr Gly Arg Leu Phe Phe Glu Phe Tyr Arg
                725                 730                 735

Leu Leu His Asp Ala Arg Pro Lys Glu Gly Asp Asp Arg Pro Phe Phe
            740                 745                 750

Trp Leu Phe Glu Asn Val Val Ala Met Gly Val Ser Asp Lys Arg Asp
            755                 760                 765

Ile Ser Arg Phe Leu Glu Ser Asn Pro Val Met Ile Asp Ala Lys Glu
            770                 775                 780

Val Ser Ala Ala His Arg Ala Arg Tyr Phe Trp Gly Asn Leu Pro Gly
785                 790                 795                 800

Met Asn Arg Pro Leu Ala Ser Thr Val Asn Asp Lys Leu Glu Leu Gln
                805                 810                 815

Glu Cys Leu Glu His Gly Arg Ile Ala Lys Phe Ser Lys Val Arg Thr
            820                 825                 830

Ile Thr Thr Arg Ser Asn Ser Ile Lys Gln Gly Lys Asp Gln His Phe
```

-continued

```
                    835                 840                 845
Pro Val Phe Met Asn Glu Lys Glu Asp Ile Leu Trp Cys Thr Glu Met
    850                 855                 860

Glu Arg Val Phe Gly Phe Pro Val His Tyr Thr Asp Val Ser Asn Met
865                 870                 875                 880

Ser Arg Leu Ala Arg Gln Arg Leu Leu Gly Arg Ser Trp Ser Val Pro
                885                 890                 895

Val Ile Arg His Leu Phe Ala Pro Leu Lys Glu Tyr Phe Ala Cys Val
                900                 905                 910
```